United States Patent [19]

Devarakonda et al.

[11] 4,102,180

[45] Jul. 25, 1978

[54] SLIDE FASTENER ENDURANCE TESTER

[75] Inventors: Vasant K. Devarakonda, Holliston; John L. Kovar, Natick, both of Mass.

[73] Assignee: The United States of America as represented by the Secretary of the Army, Washington, D.C.

[21] Appl. No.: 811,933

[22] Filed: Jun. 30, 1977

[51] Int. Cl.² ............................................. G01N 3/08
[52] U.S. Cl. ............................................. 73/91; 73/95
[58] Field of Search ............... 73/91, 95, 103, 88 F, 73/9

[56] References Cited

U.S. PATENT DOCUMENTS

| 2,493,782 | 1/1950 | Schwarz | 73/9 |
| 3,199,342 | 8/1965 | Snair et al. | 73/95 |

*Primary Examiner*—Anthony V. Ciarlante
*Attorney, Agent, or Firm*—Nathan Edelberg; Robert P. Gibson; Charles C. Rainey

[57] ABSTRACT

An apparatus and method for testing the mechanical endurance of a slide fastener by determining the number of cycles of opening and closing which the slide fastener is capable of undergoing while being subjected to preselected degrees of loading in both the transverse and longitudinal directions before jamming or other malfunctioning occurs.

9 Claims, 4 Drawing Figures

SLIDE FASTENER ENDURANCE TESTER

The invention described herein may be manufactured, used, and licensed by or for the Government for governmental purposes without the payment to us of any royalty thereon.

BACKGROUND OF THE INVENTION

This invention relates to an apparatus and method for testing the mechanical endurance of a slide fastener by determining the number of cycles of opening and closing which the slide fastener is capable of undergoing while being subjected to preselected degrees of loading in both the transverse and longitudinal directions before jamming or other malfunctioning occurs.

It has been customary in the commerical testing of slide fasteners (zippers) to follow the procedures of A.S.T.M. Standard D2061. In that standard, zipper chains and scoops are tested with respect to crosswise strength by loading a one-inch section of a zipper in a tensile testing machine to destruction, with respect to scoop pull-off by pulling a single scoop from the bead at right angles to the stringer using a tensile testing machine fitted with a specially designed fixture, and with respect to scoop slippage by determining the ability of a scoop to resist longitudinal movement along the bead of the tape with a tensile testing machine fitted with a specially designed fixture.

Federal Specification V-F-106d, entitled "Fasteners, Slide, Interlocking" provides for endurance testing of the chain of a slide fastener on a machine equipped with a reciprocating arm arranged to move the slider back and forth upon the chain a minimum of 10,000 cycles at a uniform rate of between 45 and 60 complete cycles per minute. The slider moves over a distance of approximately 5 inches for fasteners 6 inches and over in length and over a distance equal to two-thirds of the length of fasteners under 6 inches long. The stringers of the chain are not loaded transversely, nor is the slide fastener loaded longitudinally during such endurance testing.

Since in the nomral use of a slide fastener it is virtually inevitable that the slide fastener will be exposed to both transverse and longitudinal loadings of varying degrees, it is important to know how well a given slide fastener will stand up in actual use under conditions involving greater or lesser degrees of loading of the slide fastener both transversely and longitudianlly.

It is, therefore, an object of the invention to provide an apparatus for determining the endurance of a slide fastener when the slide fastener is exposed to various degrees of loading both transversely and longitudinally thereof during operation of the slide fastener, including both opening and closing thereof.

SUMMARY OF THE INVENTION

A slide fastener endurance tester which comprises means for loading a slide fastener in a variable and controllable manner both transversely and longitudinally and which determines the number of cycles of opening and closing of which the slide fastener is capable under various loadings until jamming thereof occurs. Also a method of determining the endurance capability of a slide fastener while it is loaded both transversely and longitudinally to various degrees.

DESCRIPTION OF THE PREFERRED EMBODIMENT

An important feature of our invention is the testing of the endurance of a slide fastener when it is subjected to both transverse and longitudinal loadings during cyclic operation of the slide fastener for a preselected number of opening and closing cycles or until jamming or other malfunctioning of the slide fastener occurs, the degrees of transverse and longitudinal loadings being variable.

The invention will become apparent from the following description of one embodiment thereof taken in conjunction with the accompanying drawings, in which.

Figure 1:
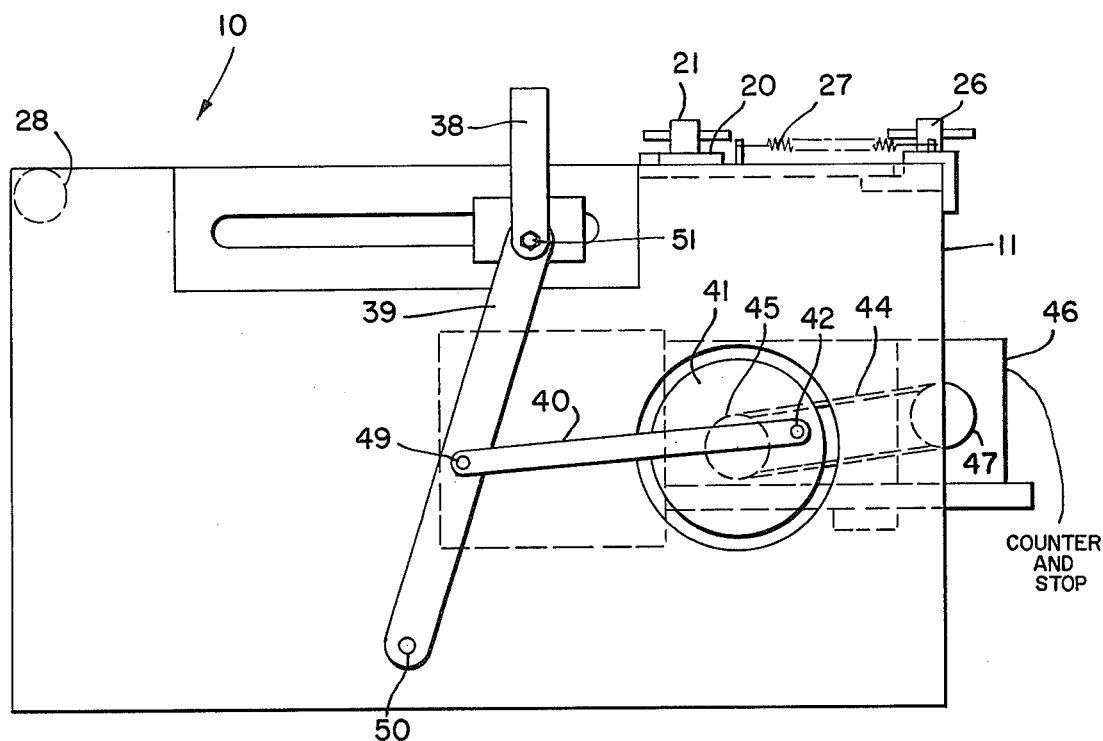
FIG. 1 is a side view in elevation of the apparatus of the invention.

In the embodiment of the invention shown in the drawings, reference numeral 10 represents the slide fastener endurance tester. The endurance tester comprises a rectangularly-shaped casing 11 for containing and supporting the working elements of the tester, which comprise means for maintaining a slide fastener 12 whose endurance is being tested in an elongated position and under both transverse and longitudinal loading, and means for reciprocatingly moving the slider 13 of the slide fastener back and forth over a preselected portion of the chain 14 of the slide fastener, and means for counting the cycles of reciprocative movement of the slider during the testing of the slide fastener.

The slide fastener endurance tester comprises a plurality of transverse loading clamps 15, preferably four pairs of such clamps, and associated transverse loading means. Each associated transverse loading means comprises a hollow tube 16, preferably cylindrical, within which a linear compression spring (not shown) is encased. A plunger 17 is connected to clamp 15 and passes freely through an opening in the end of tube 16 nearest to clamp 15 and through the coils of the compression spring to a head (not shown) which has a diameter slightly less than the inner diameter of hollow tube 16 so that the plunger 17 is able to move freely with respect to both tube 16 and the compression spring, the head thereof compressing or permitting decompressing of the spring. The opposite end of tube 16 from clamp 15 has an opening therein which is internally threaded to mate with external threads on adjusting rod 18, which is connected to a sidewall of casing 11. Tube 16 is rotatable so as to adjust the loading applied to tape 19; the closer tube 16 is to the sidewall, the greater the load that is applied to tape 19 by way of compression of the spring within the tube 16. Each pair of transverse loading clamps and associated loading elements is calibrated for loadings from zero to 5 pounds, the calibrations being located on the upper edges of plungers 17, placed so that the load being applied is indicated by the positions of the various calibrations on the plungers with respect to the ends of tubes 16 nearest to clamps 15.

The four clamps 15 on each side of the slide fastener are spaced apart so as to cover an approximately six inch portion lengthwise of the slide fastener.

The slide fastener endurance tester also comprises two pinch clamps 20, operated by wing bolts 21, which serve to hold the tapes 19 of the slide fastener apart above the length over which the slide fastener is to be tested by reciprocatingly moving slider 13, and to maintain the slide fastener in a longitudinally extended state throughout the testing thereof. Pinch clamps 20 are mounted on the ends of arms 22 which pivot at bolts 23, which connect each arm 22 with bracket 24, which is clamped to crosspiece 25 at the upper end of the endurance tester by means of wing bolts 26. Each arm 22 is under a bias pulling it outwardly toward one side or the other of the endurance tester which is applied by a spring 27, one end of each of which is attached to the corresponding arm while the other end is attached to crosspiece 25. This effectively holds the upper portions of the slide fastener, which is being tested, somewhat apart but substantially in the horizontal plane common to the plane in which the preselected portion of the slide fastener is being maintained while it is being subjected to the reciprocating motion of the slider.

The portion of the slide fastener immediately below the portion thereof being tested is maintained in the same horizontal plane as the portion being tested by means of roller 28, which is freely rotatable and extends across substantially the full width of the endurance tester, until the slide fastener turns downwardly as it passes over the top of roller 28.

Figure 4:
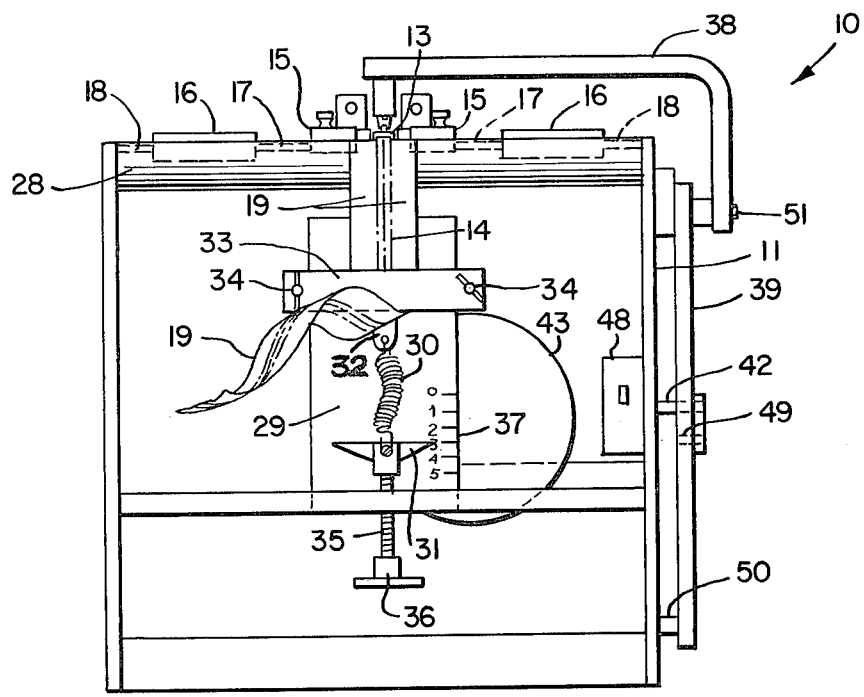
FIG. 4 is an end view in elevation of the apparatus of the invention, showing means for applying and measuring the longitudinal loading being applied to a slide fastener during testing of endurance thereof.

As shown in FIG. 4, after passing over roller 28, the slide fastener passes downwardly in front of longitudinal load gauge 29, which is graduated in pounds, or may be graduated in other units, if desired.

The longitudinal loading means comprises a spring 30 which is attached at its lower end to pointer 31 and at its upper end to a clip 32, which in turn is attached to clamp 33, which consists of a pair of flat bars between which the slide fastener passes and is held tightly clamped by tightening wing bolts 34. Pointer 31 is attached to adjusting screw 35, which is adjusted upwardly to apply less load to the slide fastener or downwardly to apply a greater load to the slide fastener in a longitudinal direction by rotating thumb screw adjustment knob 36. The longitudinal load gauge is calibrated to register in 1-pound increments from zero to 5 pounds, the applied longitudinal load being indicated by the position of pointer 31 with respect to the graduations 37 on longitudinal load gauge 29.

Figure 2:
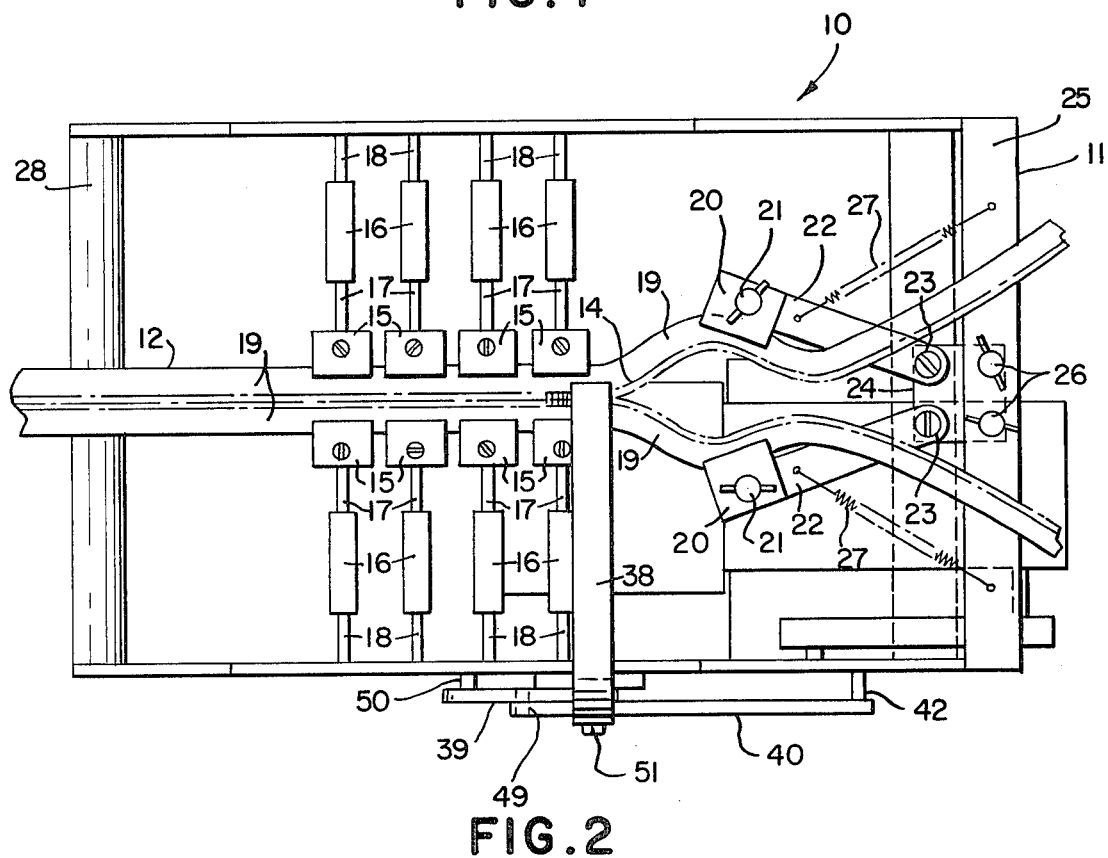
FIG. 2 is a plan view looking down on the slide fastener endurance tester from a point above the same, showing the slide fastener in a closed position.
Figure 3:
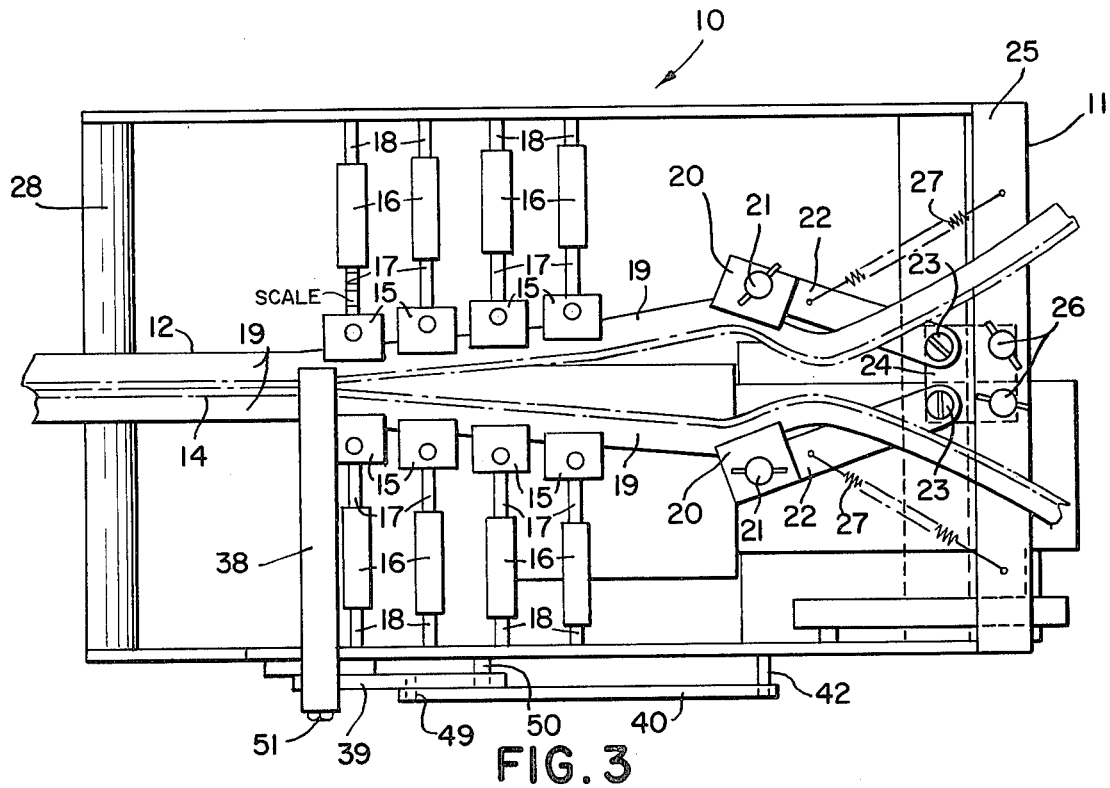
FIG. 3 is a plan view similar to FIG. 2, but showing the slide fastener in an open position.

The slider 13 of the slide fastener is reciprocatingly moved along chain 14 by reciprocating arm 38 to the free end of which the slider is clamped. As shown in FIGS. 1 and 4, reciprocating arm 38 is driven by pivoted arm 39, which is driven reciprocatively by connecting arm 40, which is driven by motor-driven flywheel 41 through an eccentric 42. The motor which drives the various elements of the slide fastener tester is generally represented by 43. A belt 44, which is driven by a pulley 45 on the shaft of the motor, drives a counter and stop 46 through pulley 47, which counter and stop registers the number of complete opening and closing cycles of the slide fastener, one revolution of the counter representing the motion of the reciprocating arm and the slider from the closed position shown in FIG. 2 to the open position shown in FIG. 3 and back to the closed position of FIG. 2. Switch 48 controls the flow of power to the motor. The counter and stop 46 is electrically coupled with the drive motor 43 so that the motor and counter will be stopped automatically after a preselected number of cycles of the reciprocating movements of the slider. Pivot points at 42, 49, 50, and 51 convert the rotary motion of motor 43 into the reciprocating motion of reciprocating arm 38 which effects the repetitive opening and closing of slide fastener 12 while it is being subjected to preselected transverse loads along the length of the chain being tested and to a preselected longitudinal load over the greater portion of the length of the slide fastener including the portion being subjected to endurance testing.

The greater the number of cycles of opening and closing to which a slide fastener can be subjected before it jams provides a very good indication of the durability of the slide fastener. Such numbers of cycles will vary according to the conditions of loading to which the slide fastener is subjected. Hence, any direct comparison between two or more slide fasteners must be based on performance under like loading conditions.

Other types of loading means may be employed in place of the types disclosed herein. Other degrees of loading, both transversely and longitudinally, may be employed. The path of movement of the slider 13 may be changed to an arc rather than a substantially straight line or plane, if desired, by modifying the cam of the tester.

It will be readily apparent that we have provided an apparatus for testing the endurance of slide fasteners such that results obtained with different slide fasteners can be more readily and objectively compared since the very important use parameters of degree of transverse loading and degree of longitudinal loading are controlled and measured during the actual endurance testing of the slide fasteners.

We wish it to be understood that we do not desire to be limited to the exact details described, for obvious modifications will occur to a person skilled in the art.

We claim:

1. In a slide fastener endurance tester comprising means for supporting a slide fastener extended longitudinally and transversely and means for reciprocatingly moving the slider of said slide fastener back and forth along a predetermined portion of the chain of said slide fastener to open and close said slide fastener, the improvement which comprises means for variably and controllably loading said slide fastener transversely thereof and means for variably and controllably loading said slide fastener longitudinally thereof while said slider is being reciprocatingly moved along said chain, and means for counting the number of cycles of said reciprocating movements of said slider along said chain.

2. A slide fastener endurance tester according to claim 1, wherein said means for variably and controllably loading said slide fastener transversely comprise a plurality of adjustably spring-biased clamps disposed in pairs lengthwise of said slide fastener, each member of a pair of said spring-biased clamps working in opposition to the other member of said pair of said spring-biased clamps so as to maintain said slide fastener transversely loaded to a predetermined degree along a segment of said predetermined portion of the chain of said slide fastener.

3. A slide fastener endurance tester according to claim 2, wherein there are four of said pairs of adjustably spring-biased clamps disposed lengthwise of said slide fastener.

4. A slide fastener endurance tester according to claim 3, wherein said means for variably and controllably loading said slide fastener longitudinally comprises a spring loading means.

5. A slide fastener endurance tester according to claim 4, wherein each of said pairs of adjustably spring-biased clamps has an adjustability from zero to about 5 pounds of transverse loading and said spring loading means for variably and controllably loading said slide fastener longitudinally has an adjustability from zero to about 5 pounds of longitudinal loading.

6. A slide fastener endurance tester according to claim 5, wherein said means for counting the number of cycles of said reciprocating movements of said slider along said chain is provided with means for stopping said means for reciprocatingly moving said slider back and forth along said predetermined portion of said chain of said slide fastener after a predetermined number of cycles of said reciprocating movements of said slider along said chain.

7. A slide fastener endurance tester according to claim 1, wherein said means for variably and controllably loading said slide fastener longitudinally comprises a spring loading means.

8. A slide fastener endurance tester according to claim 1, wherein said means for counting the number of cycles of said reciprocating movements of said slider along said chain is provided with means for stopping said means for reciprocatingly moving said slider back and forth along said predetermined portion of said chain of said slide fastener after a predetermined number of cycles of said reciprocating movements of said slider along said chain.

9. A method of determining the endurance of a slide fastener which comprises the steps of reciprocatingly moving the slider element of said slide fastener back and forth from a closed position to an open position and back to said closed position and continuing said reciprocating movement of said slider element while applying to the chain of said slide fastener known transverse and longitudinal loads and counting the number of complete cycles of the reciprocating movements of said slider until said slide fastener jams.

* * * * *